(12) United States Patent
Kostadinov et al.

(10) Patent No.: US 7,981,908 B2
(45) Date of Patent: *Jul. 19, 2011

(54) COMPOSITIONS AND METHODS FOR INHIBITING GASTRIC ACID SECRETION

(75) Inventors: Aleksey Kostadinov, Rehovot (IL); David Ayelet, Negev (IL); Sabina Glozman, Rehovot (IL); Tal Atarot, Tel Mond (IL)

(73) Assignee: Vecta, Ltd., Ra'annana (IL)

( * ) Notice: Subject to any disclaimer, the term of this patent is extended or adjusted under 35 U.S.C. 154(b) by 218 days.

This patent is subject to a terminal disclaimer.

(21) Appl. No.: 12/120,599

(22) Filed: May 14, 2008

(65) Prior Publication Data

US 2008/0248109 A1  Oct. 9, 2008

Related U.S. Application Data

(63) Continuation-in-part of application No. 11/191,688, filed on Jul. 27, 2005, now Pat. No. 7,803,817.

(60) Provisional application No. 60/679,664, filed on May 11, 2005, provisional application No. 60/917,726, filed on May 14, 2007.

(51) Int. Cl.
*A61K 31/4439* (2006.01)
*A61K 31/194* (2006.01)

(52) U.S. Cl. .................................. 514/333; 514/574

(58) Field of Classification Search .................. None
See application file for complete search history.

(56) References Cited

U.S. PATENT DOCUMENTS

| | | | |
|---|---|---|---|
| 4,255,431 A | 3/1981 | Junggren et al. | |
| 4,767,627 A | 8/1988 | Caldwell et al. | |
| 4,786,505 A | 11/1988 | Lovgren et al. | |
| 4,853,230 A | 8/1989 | Lovgren et al. | |
| 5,137,729 A | 8/1992 | Kuroya et al. | |
| 5,238,686 A * | 8/1993 | Eichel et al. | 424/461 |
| 5,559,152 A | 9/1996 | Komissarova et al. | 514/557 |
| 5,731,002 A | 3/1998 | Olovson et al. | 424/484 |
| 5,750,531 A | 5/1998 | Lee et al. | |
| 5,800,832 A | 9/1998 | Tapolsky et al. | |
| 5,840,737 A | 11/1998 | Phillips | 514/338 |
| 6,093,738 A | 7/2000 | Karimian et al. | |
| 6,159,498 A | 12/2000 | Tapolsky et al. | |
| 6,228,400 B1 | 5/2001 | Lee et al. | 424/489 |
| 6,296,876 B1 | 10/2001 | Odidi | 424/480 |
| 6,489,346 B1 | 12/2002 | Phillips | 514/338 |
| 6,645,988 B2 | 11/2003 | Phillips | 514/338 |
| 6,699,885 B2 | 3/2004 | Phillips | 514/338 |
| 6,780,882 B2 | 8/2004 | Phillips | 514/338 |
| 6,815,414 B2 | 11/2004 | Chowers et al. | 514/8 |
| 7,211,568 B2 | 5/2007 | Liu et al. | |
| 7,271,146 B2 | 9/2007 | Glozman | |
| 2001/0020005 A1 | 9/2001 | Chowers et al. | |
| 2003/0049204 A1 | 3/2003 | Leyland-Jones | 424/9.1 |
| 2004/0067875 A1 | 4/2004 | Lai et al. | 514/6 |
| 2004/0106634 A1 | 6/2004 | Satoh et al. | 514/275 |
| 2004/0248942 A1 | 12/2004 | Hepburn | 514/338 |
| 2005/0181052 A1 | 8/2005 | Patel et al. | |
| 2005/0232992 A1 | 10/2005 | Devane et al. | 424/468 |
| 2005/0239845 A1 | 10/2005 | Proehl et al. | |
| 2006/0135406 A1 | 6/2006 | Glozman et al. | |
| 2006/0257467 A1 | 11/2006 | Kostadinov et al. | |

FOREIGN PATENT DOCUMENTS

| | | |
|---|---|---|
| EP | 05129 A1 | 10/1979 |
| EP | 124495 A2 | 11/1984 |
| EP | 166287 A1 | 1/1986 |
| EP | 174726 A1 | 3/1986 |
| EP | 259174 A1 | 3/1988 |
| EP | 322133 A1 | 6/1989 |
| EP | 404322 A1 | 12/1990 |
| EP | 1 087 783 | 4/2001 |
| EP | 1917959 A1 | 5/2008 |
| EP | 07804623 | 10/2009 |
| GB | 2163747 A | 3/1986 |
| GB | 2 394 895 | 5/2004 |
| RU | 2240110 C2 | 11/2004 |
| WO | WO-9006925 A1 | 6/1990 |
| WO | WO-9119711 A1 | 12/1991 |
| WO | WO-9119712 A1 | 12/1991 |
| WO | WO 94/01099 | 1/1994 |
| WO | WO-9427988 A1 | 12/1994 |
| WO | WO-9501977 A1 | 1/1995 |
| WO | WO-9725030 A1 | 7/1997 |
| WO | WO 99/65513 | 12/1999 |
| WO | WO-0078293 A1 | 12/2000 |
| WO | WO 01/22985 | 4/2001 |

(Continued)

OTHER PUBLICATIONS

European Examination Report, Application No. 07804623.2 Feb. 9, 2010.

(Continued)

*Primary Examiner* — Phyllis G. Spivack
(74) *Attorney, Agent, or Firm* — Mintz Levin Cohn Ferris Glovsky and Popeo, P.C.; Ivor R. Elrifi; Christina K. Stock, Esq.

(57) ABSTRACT

The present invention is related to novel oral compositions comprising an irreversible gastric $H^+/K^+$-ATPase proton pump inhibitor (PPI) as a gastric acid secretion inhibitor and one or more small carboxylic acid molecules as parietal cell activators in the gastric lumen. Unexpectedly, the compositions of the present invention are capable of enhancing the anti-acid activity of PPI in the stomach. The present invention further relates to a method of using such compositions to reduce gastric acid secretion in a mammal.

22 Claims, 3 Drawing Sheets

FOREIGN PATENT DOCUMENTS

| WO | WO-0151050 A1 | 7/2001 |
|----|----|----|
| WO | WO 2005/065664 | 7/2005 |
| WO | WO-2006120500 A1 | 11/2006 |
| WO | WO-2008012621 A2 | 1/2008 |

OTHER PUBLICATIONS

International Search Report from PCT/IB2009/006176 dated Dec. 8, 2009.
Chand et al., "Sleep dysfunction in patients with gastro-oesophageal reflux disease: prevalence and response to GERD therapy, a pilot study", *Aliment Pharmacol. Ther. 2004*, 20:969-974 (2004).
Chen et al., "Sleep Symptoms and Gastroesophageal Reflux", *J. Clin. Gastroenterol.*, 42(1):13-17 (2008).
Hatlebakk et al., "Pharmacokinetic Optimisation in the Treatment of Gastro-Oesophageal Reflux Disease", *Clin. Pharmacokinet.*, 31(5):386-406 (1996).
International Search Report for PCT/IB07/01078 dated Apr. 9, 2009.
International Search Report for PCT/IB05/02223 dated Mar. 28, 2006.
Morii et al., "The Potency of Substituted Benzimidazoles such as E3810, Omeprazole, Ro 18-5364 to Inhibit Gastric $H^+,K^+$-ATPase is Correlated with the Rate of Acid-Activation of the Inhibitor", *Biochem. Pharmacol.*, 39(4):661-667 (1990).
Sachs, G., "Improving on PPI-based therapy of GORD", *Eur. J. Gastroenterol. Hepatol.*, 13(Suppl. 1):S35-S41(2001).
Scarpignato et al., "Acid Suppression Therapy: Where Do We Go from Here?" *Dig. Dis.*, 24:11-46 (2006).
Shaker et al., "Nighttime Heartburn Is an Under-Appreciated Clinical Problem That Impacts Sleep and Daytime Function: The Results of a Gallup Survey Conducted on Behalf of the American Gastroenterological Association", *Am. J. Gastroenterol.*, 98(7):1487-1493 (2003).
Tytgat, G.N., "Shortcomings of the first-generation proton pump inhibitors", *Eur. J. Gastroenterol. Hepatol.*, 13(Suppl. 1):S29-S33 (2001).
Written Opinion of the International Search Authority for PCT/IB05/02223 dated Mar. 28, 2006.
Written Opinion of the International Search Authority for PCT/IB07/01078 dated Apr. 9, 2009.
Yau et al., "A comparison of omeprazole and ranitidine for prophylaxis against aspiration pneumonitis in emergency Caesarean section", *Anaesthesia*, 47:101-104 (1992).
Ammar, D. A., et al., "Syntaxin 3 is required for camp-induced acid secretion: streptolysin O-permeabilized gastric gland model," *American Journal of Physiology—Gastrointestinal and Liver Physiology*, 282:G23-G33 (2002).
Ayalon, A. et al., "Does Luminal Gastrin Stimulate Gastric Acid Secretion?" *Am. J. Surg.*, 141:94-97 (1981).
De Graef, J. et al., "Influence of the Stimulation State of the Parietal Cells on the Inhibitory Effect of Omeprazole on Gastric Acid Secretion in Dogs," *Gastroenterology*, 91:333-337 (1985).
Fiddian-Green, R.G. et al., "A physiological role for luminal gastrin?" *Surgery*, 83(6):663-668 (1978).
Hunt, J. N. et al., "The Effect of Citric Acid and Its Sodium Salts in Test Meals on the Gastric Outputs of Acid and of Chloride," *J. Physiol.*, 230(1):171-184 (1973).
Kuroda et al., "Inhibitory Effect of Fumaric Acid and Dicarboxylic Acids on Gastric Ulceration in Rats", *Arch. Int. Pharmacodyn.*, 226:324-330 (1977).
Maliuk et al, "Effect of Succinate Sodium on the Acid Forming and Motor Function of the Stomach in Patients with Tuberculosis", *rachebnoe Delo*, 10:60-62 (1981). Summary Only.
Morrell, M. T. et al., "Absorption of Pentagastrin from Gastrointestinal Tract in Man," *Lancet*, 2(7937):712 (1975).
Nagata et al., "Inhibitory Action of Lansoprazole and Its Analogs Against *Helicobacter pylori*: Inhibition of Growth is Not Related to Inhibition of Urease," *Antimicrobial Agents and Chemotherapy*, 39(2):567-570 (1995).
Nobuhara et al., "Vinegar is a Dietary Mild Irritant to the Rat Gastric Mucosa", *Japanese Journal of Pharmacology*, 41:101-108 (1986).
Pokrovsky, A. A. et al., "On the Role of Succinate in Energy Supply of the Hydrochloric Acid Secretion in the Gastric Mucosa", *Journal of Physiology*, 10:1567-1573 (1973). Abstract Only.
Teyssen et al., "Maleic and Succinic Acid as Stimulants of Acid Production in Isolated Native Rat Gastric Parietal Cells", *Esophageal, Gastric and Duodenal Disorders*, G1456:A333 (Apr. 1999).
Teyssen, S. et al., "Maleic Acid and Succinic Acid in Fermented Alcoholic Beverages Are the Stimulants of Gastric Acid Secretion," *The Journal of Clinical Investigation*, 103(5):707-713 (1999).
Merritt, A.M., "The Equine Stomach: A Personal Perspective (1963-2003)", 49th Annual Convention of the American Association of Equine Practitioners, www.ivis.org, Nov. 21, 2003.

* cited by examiner

COMPOSITIONS AND METHODS FOR INHIBITING GASTRIC ACID SECRETION

This application is a continuation-in-part of U.S. application Ser. No. 11/191,688 filed on Jul. 27, 2005, which claims the benefit of U.S. Provisional Application No. 60/679,664 filed May 11, 2005, and this application also claims the benefit of U.S. Provisional Application No. 60/917,726 filed May 14, 2007, the content of each the above cited applications of which is expressly incorporated herein by reference thereto.

FIELD OF THE INVENTION

The present invention relates to novel oral compositions for inhibition of gastric acid secretion comprising a proton pump inhibitor in conjunction with one or more small monocarboxylic, dicarboxylic or tricarboxylic acids which are in a form for release in the stomach and in an amount sufficient to reduce gastric acid secretion in conjunction with the PPI. The present invention further relates to a method of using such compositions to reduce gastric acid secretion in a mammal.

BACKGROUND OF THE INVENTION

A wide number of pathological conditions are characterized by the need to suppress gastric acid secretion. Such conditions include, but are not limited to Zollinger/Ellison syndrome (ZES), gastroesophageal reflux disease (GERD), peptic ulcer disease, duodenal ulcers, esophagitis, and the like. Conditions such as peptic ulcers can have serious complications and represent some of the most prevalent diseases in industrialized nations.

Presently, the main therapies employed in the treatment of GERD and peptic ulcer diseases include agents for reducing the stomach acidity, for example by using the histamine $H_2$-receptor antagonists or proton pump inhibitors (PPIs). PPIs act by inhibiting the parietal cell $H^+/K^+$ ATPase proton pumps responsible for acid secretion from these cells. PPIs, such as omeprazole, and its pharmaceutically acceptable salts are disclosed for example in EP 05129, EP 124495 and U.S. Pat. No. 4,255,431.

PPI agents are acid-labile pro-drugs that are usually administered in enteric-coated granules and are weak bases. Following absorption in the small intestine, PPIs preferentially accumulate within the acid milieu of the acid-secreting parietal cells. The acid environment within the acid milieu of parietal cells causes the conversion of the pro-drugs into the active sulfenamides, which are the active agents that bind and inhibit the parietal cell $H^+/K^+$ ATPase pumps. Thus, pre-activation of parietal cells is required for the conversion of PPIs to its active protonated form. The pre-activation of parietal cells is usually achieved by meal ingestion that initiates gastrin-dependent parietal cell activation. Indeed, patients are instructed to take PPI one hour prior to meal intake in order to ensure that parietal cells are activated when the PPI reaches the parietal cells via blood stream.

Despite their well-documented efficacy, PPIs have notable limitations. The conversion of PPI to its active form requires pre-activation of parietal cells. The pre-activation of parietal cells is usually achieved with food. Thus, the PPI must be taken prior to ingestion of food in order to synchronize between the pre-activation of parietal cells and PPI absorption into the blood. Furthermore, PPIs have a relatively slow onset of pharmacological action and may require several days to achieve maximum acid suppression and symptom relief, limiting their usefulness in on-demand GERD therapy (Sachs G, Eur J Gastroenterol Hepatol. 2001; 13 Suppl 1:S35-41).

Moreover, once daily PPI administration fails to provide 24-h suppression of gastric acid while nocturnal acid breakthrough that leads to heartburn pain in GERD patients occurs even with twice-daily dosing of PPIs (Tytgat G N, Eur J Gastroenterol Hepatol. 2001; 13 Suppl 1:S29-33; Shaker R. et al., Am. J. of Gastroenterology, 98 (7), 2003). Thus, an improvement of PPI-mediated activity, especially at nighttime, is a well-recognized challenge in gastroenterology. (Scarpignato C. et al Dig. Dis 2006; 24:11-46.

Maleic acid and succinic acid, chemically characterized as four-carbon dicarboxylic acids, are known as powerful stimulants of gastric acid secretion (Teyssen et al., J. Clin Invest. 1999 103(5): 707-713). Teyssen et al. studied the stimulation of gastric acid secretion in fermented alcoholic beverages produced by fermentation (e.g., beer and wine). Interestingly, maleic acid and succinic acid extracted from fermented alcoholic beverages were found to stimulate gastric acid output in humans as that produced by beer, champagne, wine, and pentagastrin (a powerful exogenous stimulus to induce acid secretion), but without gastrin being their mediator of action.

U.S. Pat. No. 5,559,152 discloses that a mixture of succinic acid and citric acid in the dose of 3.5 mg/kg is capable of inducing gastric acid secretion in dogs as reflected by significant reduction in the pH of the gastric juice measured on an empty stomach 40 min following drug administration. This patent further discloses that succinic and citric acid stimulate acid secretion in healthy human volunteers.

Pokrovskiy et al. (Physiologicheskiy Z'urnal 10:1567-1573, 1973) also disclosed that molecules involved in the mitochondrial respiration circle (krebs cycle) such as pyruvate, succinate, alpha-ketoglutarate, malate or glucose may stimulates proton secretion in ex vivo model of frog mucosa.

U.S. Pat. Nos. 6,489,346; 6,645,988; and 6,699,885; to Phillips jointly the "Phillips patents") disclose pharmaceutical compositions and methods of treating acid-caused gastrointestinal disorders using oral compositions consisting of a PPI, at least one buffering agent and specific parietal cell activators. The parietal cell activators disclosed in the Phillips patents include, for example, chocolate, sodium bicarbonate, calcium, peppermint oil, spearmint oil, coffee, tea and colas, caffeine, theophylline, theobromine and amino acids residues.

The development of an effective treatment for pathologies in which inhibition of gastric acid secretion is required would fulfill a long felt need. Despite the wide-spread use of PPIs, a need still exist for increasing the PPI efficacy, e.g., prolonged effect to control night time acid breakthrough, greater effect at reduced dosage and meal-independent administration. Applicants' invention disclosed herein meets many of these long felt needs.

SUMMARY OF THE INVENTION

It is the object of the present invention to provide PPI-based compositions with enhanced activity in inhibition of gastric acid secretion.

In one preferred embodiment, the present invention relates to a multiple unit pharmaceutical composition comprising as active ingredients a pharmaceutically effective amount of: (i) succinic acid particles or any salts thereof; and (ii) an enteric-coated proton pump inhibitor (PPI), wherein the succinic acid particles are released in the stomach and are in an amount sufficient to reduce gastric acid secretion in conjunction with the PPI and wherein the enteric-coated PPI and the succinic acid particles are physically separated within the multiple unit composition. In one embodiment, the succinic acid particles are encapsulated in an internal capsule, the internal capsule is encapsulated within an external capsule which contains the enteric-coated PPI. In another embodiment, the enteric-coated PPI is encapsulated in an internal capsule, the internal capsule is encapsulated within an external capsule which contains the succinic acid particles. Physical separation between the enteric-coated PPI and the succinic acid particles is advantageous since it prevents interaction between the two components in the formulation and thus improves the formulation stability.

The present invention relates generally to compositions comprising a substituted benzimidazole $H^+/K^+$-ATPase proton pump inhibitor (PPI) in a delayed release form for release in the small intestine and one or more saturated or non-saturated small monocarboxylic, dicarboxylic or tricarboxylic acids, salts or derivatives thereof which are in a form for release in the stomach, and are in an amount sufficient to reduce gastric acid secretion in conjunction with the PPI. Preferred acids to be used in conjunction with the PPI are small monocarboxylic, dicarboxylic or tricarboxylic acid involved in the mitochondrial respiration circle (krebs cycle). Unexpectedly, the compositions of the present invention are capable of enhancing the anti-acid activity of PPI in the stomach. Activation of parietal cell's proton pumps with the carboxylic acid molecules of the invention as a pharmacologic stimulus, eliminates the therapeutic dependence of PPI therapy on careful timing with food. This enables an effective bedtime administration to GERD patients which are not allowed to eat before bedtime. The present compositions may be used for treating a subject suffering from chronic or acute disorders in which suppression of acid secretion in the stomach is required.

The substituted benzimidazole proton pump inhibitors according to the present invention are compounds that inhibit the activity of the $H^+/K^+$-adenosine triphosphatase (ATPase) proton pump in the gastric parietal cells. In its pro-drug form, the PPI is non-ionized and therefore is capable of passing through the cellular membrane of the parietal cells. Once reaching the parietal cells, the non-ionized PPI moves into the acid-secreting portion of activated parietal cells, the secretory canaliculus. The PPI trapped in the canaliculus becomes protonated, thus converted to the active sulfenamide form that can form disulfide covalent bonds with cysteine residues in the alpha subunit of the proton pump, thereby irreversibly inhibiting the proton pump.

The present invention is based on the inventors surprising discovery that small monocarboxylic, dicarboxylic or tricarboxylic acid molecules involved in the mitochondrial respiration circle (krebs cycle) which are in a form for release in the stomach can enhance the activity of proton pump inhibitors in inhibiting gastric acid secretion. Without being bound by theory, such molecules accelerate the activation of the parietal cells in the stomach and thus maximizing the inhibition of the pumps by the PPI.

The compositions of the present invention exhibit an advantage over the known PPI-based compositions aimed to reduce gastric acid secretion. The present compositions exhibit anti-acid activity in the stomach in a meal-independent manner, since meal is no more required following PPI ingestion. Thus, the combined active agents of the present compositions provide an effective solution for bed-time PPI administration in GERD patients that are instructed not to ingest food at and several hours before bed-time.

The compositions according to the present invention may comprise any small monocarboxylic, dicarboxylic or tricarboxylic acids, salts or derivatives thereof in the form for release in the stomach and in an amount sufficient to reduce gastric acid secretion in conjunction with the PPI. Preferred carboxylic acids are small saturated or non-saturated monocarboxylic, dicarboxylic or tricarboxylic acids involved in krebs cycle. Most preferred small dicarboxylic acids are saturated or non-saturated dicarboxylic or tricarboxylic acids such as maleic acid, succinic acid or citric acid, or any derivative or salts thereof. Also included within the scope of the present invention are other small carboxylic acid molecules involved in krebs cycle such as for example pyruvate, $\alpha$-ketoglutarate, succinyl-CoA, fumarate, or oxaloacetate.

The compositions according to the present invention are preferably oral compositions, however, parenteral administration of PPI (such as intravenous or buccal administration) in conjunction with the acid molecules in oral form for release in the stomach is also included in the scope of the present invention. The active ingredients of the present invention may be formulated in a single oral dosage form, preferably a solid dosage form. In this case, the release of the PPI in the small intestine and the small carboxylic acids in the stomach is adjusted so as to achieve synchronization between the effect of the small carboxylic acids and the absorption of PPI in blood. Thus, in one embodiment the PPI and the small carboxylic acids according to the present invention are formulated as multi-layered tablets, effervescent tablets, powder, pellets, granules, hard and soft gelatin capsules comprising multiple beads, capsule within a capsule (in which the small carboxylic acid particles such as succinic acid and the PPI are physically separated) Liquid dosage forms such as solutions, emulsions, foams and suspensions may be used as well.

According to one embodiment, the solid dosage form of the present invention is a capsule or a multi-layered tablet containing PPI particles coated with either enteric pH-dependent release polymers or non-enteric time-dependent release polymers for release in the small intestine and particles of the small carboxylic acids according to the present invention in a form for release in the stomach. In order to ensure that the activity of the small carboxylic acids in the stomach is synchronized with the absorption of the PPI in the proximal part of the small intestine, the single oral dosage form may comprise small carboxylic acids beads coated with a time-dependent release polymer that extends the releasing time in the stomach. Specifically, the delay in the release of small carboxylic acids in the stomach permits the synchronization between the activity of the carboxylic acids and the absorption of the PPI in the blood. Extending or delaying the release of the small carboxylic acids in the stomach may be achieved by using solid forms of the small carboxylic acids (e.g crystalline powders) and/or polymer coating of the small carboxylic acids and/or by the final formulation properties (e.g. release of the small carboxylic acids from a matrix or a capsule).

The active ingredients of the present invention may also be formulated in separate dosage forms. For example, the small carboxylic acids according to the present invention may be formulated in an oral suspension or a solid dosage form such as capsules, tablets, or effervescent tablets in the form for release in the stomach and the PPI may be formulated in a separate solid dosage form, preferably capsules or tablets comprising beads with enteric pH-dependent release polymers or non-enteric time-dependent release polymers for release in the small intestine. The separate dosage forms may be provided as a kit containing beads of the small carboxylic acids in one dosage form and the beads of PPI in a separate dosage form. In this case, the small carboxylic acids are administered in conjunction with the PPI so that there is at least some chronological overlap in their physiological activity. The PPI and the small carboxylic acids can be administered simultaneously and/or sequentially.

The PPI may also be formulated in a dosage form suitable for parenteral administration such as intravenous administration, buccal administration and subcutaneous injection. Thus, PPI may be formulated for transmucosal (buccal) delivery and the small carboxylic acids may be formulated for oral (tablets, capsule) delivery in the form for release in the stomach, in either separate or single-unit dosage form.

In one embodiment, the invention is directed to a pharmaceutical composition comprising a first and second unit. The first unit typically comprises one or more small carboxylic acid molecules, or any salts thereof and the second unit comprises an enteric coated proton pump inhibitor (PPI), wherein the small carboxylic acid molecules and enteric-coated PPI are physically separated. Preferably, the first unit is designed to release at least 50% of the small carboxylic acid molecules in the stomach in amounts sufficient to activate parietal cells of a subject, preferably a human subject, and the carboxylic acid molecules in conjunction with the PPI reduce gastric acid secretion in the stomach.

In another embodiment, the invention is directed to a pharmaceutical composition comprising as active ingredients (i) one or more small carboxylic acid molecules, or any salts thereof which activate parietal cells and (ii) an enteric coated irreversible gastric $H^+/K^+$-ATPase proton pump inhibitor (PPI), wherein the ratio between the small carboxylic acid molecules and the PPI is from about 20:1 to about 2:1, more preferably about 10:1 to about 5:1. The small carboxylic acid molecules advantageously are substantially released in the stomach in an amount sufficient to activate parietal cells located in the gastric lumen of a subject.

In yet another illustrative embodiment, the invention is directed to a pharmaceutical composition comprising as active ingredients (i) one or more small carboxylic acid molecules, or any salts thereof which activate parietal cells in a delayed release form and (ii) an enteric coated irreversible gastric $H^+/K^+$-ATPase proton pump inhibitor (PPI), wherein the carboxylic acid molecules are in a form for delayed release in the stomach. In this embodiment, the small carboxylic acid molecules are substantially released in the stomach in an amount sufficient to activate parietal cells, but the release is sufficiently delayed in the stomach to synchronize activation of the parietal cells with the absorption of the PPI in the small intestine to increase the effectiveness of the PPI. In this embodiment, the release of the small carboxylic acid molecule in the stomach is preferably delayed by between 10 to 80 minutes to synchronize the release with absorption of the PPI in the blood and preferably at least 50% of the small carboxylic acid molecules are released in the stomach. The ratio between the small carboxylic acid molecules and the PPI is also preferably from about 20:1 to about 2:1. It is preferred that at least 50% of parietal cells in the stomach are activated by the small carboxylic acid molecules.

In another embodiment, the present invention is directed to a method of treating a subject suffering from a disorder in which suppression of gastric acid secretion is required or a disorder normally treated by suppression of gastric acid secretion. The method comprising administering to the subject a pharmaceutical compositions of the invention described herein, for example a composition comprising a delayed release PPI in conjunction with one or more small carboxylic acids in the form for substantial release in the stomach.

The compositions of the present invention may be used for preventing or treating pathologies in a mammal in which inhibition of gastric acid secretion is required. Preferably the mammal is human. The compositions of the present invention are effective both in treating the pathologies and in minimizing the risk of development of such pathologies before onset of symptoms.

The pharmaceutical compositions of the present invention may be used in a wide number of pathological conditions that are treated by suppression of gastric acid secretion. Such conditions include, but are not limited to Zollinger/Ellison syndrome (ZES), gastroesophageal reflux disease (GERD), nocturnal acid breakthrough, esophagitis, peptic ulcer diseases, duodenal ulcers, gastrointestinal bleeding such as non-variceal upper gastrointestinal bleeding, stress related mucosal bleeding, bleeding peptic ulcers, gastritis and gastric erosions, dyspepsia, NSAID-induced gastropathy, and the like.

The present invention also includes a pharmaceutical kit, preferably an oral pharmaceutical kit. The kit typically comprises as active ingredients a pharmaceutically effective amount of: (i) one or more small carboxylic acids according to the present invention; and (ii) a substituted benzimidazole $H^+/K^+$-ATPase proton pump inhibitor. In one embodiment, the active ingredients are formulated in separate dosage unit forms. The kit may be used to treat or prevent a disorder in a subject in which suppression of gastric acid secretion is required by administering to a subject the active ingredients. The one or more small carboxylic acids are typically administered simultaneously, prior to or following the administration of the PPI. The kit may further comprise an antibiotic effective against bacteria residing in the stomach, specifically an antibiotic/s or anti-bacterial for the treatment of ulcers associated with *Helicobacter* sp infection. The kit may further comprise prokinetic agents, alginates, non-steroidal anti-inflammatory drugs (NSAID) and other anti-reflux agents (e.g baclofen).

These and further embodiments will be apparent from the detailed description and examples that follow.

DETAILED DESCRIPTION OF THE INVENTION

Figure 1:
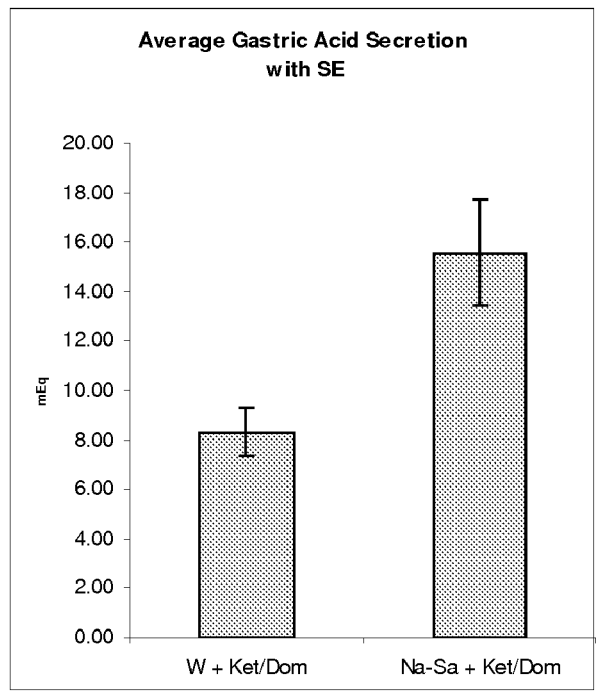
FIG. 1 demonstrates that succinic acid is capable of inducing gastric acid secretion in rats.

The compositions of the present invention provide a unique combination of active agents that increase the efficacy of the PPI in inhibiting gastric acid secretion without the requirement of timed food ingestion. The efficacy of the PPI is increased by activation of parietal cell's proton pumps with the carboxylic acid molecules of the invention.

In one embodiment, the carboxylic acid molecule, e.g., succinic acid, activates at least 50% of the parietal cells in the stomach, preferably at least 70% of the parietal cells in the stomach and more preferably at least 80% of the parietal cells in the stomach.

The compositions of the present invention may be used for preventing or treating pathologies or symptoms in a mammal in which inhibition of gastric acid secretion is required. The compositions of the present invention are effective both in treating the pathologies and in minimizing the risk of development of such pathologies before onset. Such pathologies include for example: reflux esophagitis, gastritis, duodenitis, gastric ulcer, duodenal ulcer, gastrointestinal bleeding such as non-variceal upper gastrointestinal bleeding, stress related mucosal bleeding and bleeding peptic ulcers. Furthermore, the compositions of the present invention may be used for treatment or prevention of other gastrointestinal disorders where gastric acid inhibitory effect is desirable, e.g. in patients on nonsteroidal anti-inflammatory drugs (NSAID) therapy (including low dose aspirin), in patients with Non Ulcer Dyspepsia, in patients with symptomatic gastro-esophageal reflux disease (GERD) and nocturnal acid breakthrough, and in patients with gastrinomas. They may also be used in patients in intensive care situations, in patients with acute upper gastrointestinal bleeding, in conditions of pre- and postoperatively to prevent aspiration of gastric acid and to prevent and treat stress ulceration. Further, they may be useful in the treatment of *Helicobacter* infections and diseases related to these. Other conditions well suited for treatment include, but are not limited to Zollinger-Ellison syndrome (ZES), Werner's syndrome, and systemic mastocytosis.

The compositions of the present invention may specifically be used in treating gastro-esophageal reflux disease (GERD) patients. GERD is a clinical manifestation of abnormal acid reflux of gastric contents, mainly acidic into the esophagus, resulting in irritation or injury of the esophageal mucosa. It is increasingly recognized that, in some cases, acid reflux extends beyond the esophagus into the pharynx, from where the acidic refluxate may cause injury in the throat, larynx, lungs, teeth, ears or sinuses (see for example Chand et al. 2004 *Aliment Pharmacol Ther,* 20, 969-974, 2004). Reflux is thought to result from impairment of the normal anti-reflux barrier between the stomach and the esophagus. The canonical symptoms of GERD include heartburn and acid regurgitation (see for example Chen et al., *J Clin Gastroenterol,* 42, 13-17, 2008). Heartburn and other GERD symptoms experienced during the night commonly cause sleep disturbances as well, including arousal from sleep, increased wakefulness and overall poor sleep quality (see for example Chand et al. 2004 *Aliment Pharmacol Ther,* 20, 969-974, 2004). During sleep, the esophageal mucosal response to acid contact is substantially altered, which renders the patient less capable of producing a prompt physiological response to an acid reflux event. Nighttime acid reflux is commonly associated with nighttime heartburn, regurgitation, coughing and wheezing with subsequent sleep disturbances.

The active compounds in conjunction with PPI are preferably one or more small monocarboxylic, dicarboxylic or tricarboxylic acids, or any active derivative or salt thereof. Preferred acid molecules are small carboxylic acids involved in krebs cycle. Specific preferred acid molecules are saturated aliphatic and non-saturated dicarboxylic acids that may be used as a parietal cell activator according to the present invention. Small aliphatic dicarboxylic acids are represented by the general formula: $HO_2C-(CH_2)_n-CO_2H$ (where n=0 to 5). Specific small saturated aliphatic dicarboxylic acids are Oxalic (n=0), Malonic (n=1), Succinic (n=2), Glutaric (n=3), Adipic (n=4) and Pimelic (n=5) Acids. Preferred aliphatic dicarboxylic acids to be used as parietal cell activators according to the present invention are aliphatic dicarboxylic acids having from 2 to 6 carbon atoms, more preferably 4 carbon atoms such as succinic acid. Preferred non-saturated dicarboxylic acids to be used according to the present invention are the four carbon maleic acid and fumaric acid. Instead of the free dicarboxylic acids, corresponding dicarboxylic acid derivatives or salts may be used, for example dicarboxylic acid esters, amides, halides, or dicarboxylic anhydrides or salts. Also included within the scope of the present invention are small carboxylic acid molecules involved in the mitochondrial respiration circle (krebs cycle) such as for example pyruvate, citrate, fumarate, α-ketoglutarate, succinyl-CoA or oxaloacetate.

The compositions of the present invention comprise one or more small carboxylic acids or an analog thereof in the form for release in the stomach and in an effective amount to achieve a therapeutic effect in conjunction with the PPI without undue adverse side effects. The standard approximate amount of the small carboxylic acids present in the compositions such as succinic acid is preferably in an amount of 1-2500 mg, more preferably 10-1000 mg, and most preferably 200-600 mg.

The compositions of the present invention are designed so that the small carboxylic acid such as succinic acid is in the form for release in the stomach. In various embodiments, at least 50% of the small carboxylic acid is released in the stomach, preferably at least 70% of the small carboxylic acid is released in the stomach, and more preferably at least 90% of the small carboxylic acid is released in the stomach.

In various embodiments, at least 100 mg of the small carboxylic acid, such as, succinic acid, is released in the stomach, preferably at least 150 mg of the small carboxylic acid is released in the stomach, and more preferably at least 200 mg of the small carboxylic acid is released in the stomach. In one preferred non-limiting embodiment at least 300 mg of succinic acid are released in the stomach, preferably in a delayed manner in order to synchronize the release of succinic acid in the stomach with the release and absorption of the PPI in the small intestine.

Any pharmaceutically acceptable salt of small carboxylic acids may be used in the present invention. Examples of such salts are in particular, sodium salts, disodium salts, calcium salts, magnesium salts and potassium salts as well as their known hydrates such as sodium hexahydrate.

In one preferred embodiment, the composition of the present invention comprises one or more aliphatic tricarboxylic acids, preferably citric acid in combination with the one or more dicarboxylic acids. The standard approximate amount of one or more tricarboxylic acids present in the compositions is preferably in an amount of 1-1000 mg, more preferably 10-1000 mg, and most preferably 50-200 mg.

The compositions of the present invention further comprise a PPI that acts as an irreversible inhibitor of the gastric $H^+/K^+$-ATPase proton pump. The PPI used in the present invention can be any substituted benzimidazole compound having $H^+$, $K^+$-ATPase inhibiting activity. For the purposes of this invention, the term "PPI" shall mean any substituted benzimidazole possessing pharmacological activity as an inhibitor of $H^+$, $K^+$-ATPase, including, but not limited to, omeprazole, lansoprazole, pantoprazole, rabeprazole, dontoprazole, perprazole (s-omeprazole magnesium), habeprazole, ransoprazole, pariprazole, tenatoprazole and leminoprazole in neutral form or a salt form, a single enantiomer or isomer or other derivative or an alkaline salt of an enantiomer of the same.

Examples of gastric H+/K+-ATPase proton pump inhibitors that may be used in the present invention are disclosed for example in U.S. Pat. No. 6,093,738 that describes novel thiadiazole compounds that are effective as proton pumps inhibitors. European Patent Nos. 322133 and 404322 disclose quinazoline derivatives, European Patent No. 259174 describes quinoline derivatives, and WO 91/13337 and U.S. Pat. No. 5,750,531 disclose pyrimidine derivatives, as proton pump inhibitors. Suitable proton pump inhibitors are also disclosed for example in EP-A1-174726, EP-A1-166287, GB 2 163 747 and WO90/06925, WO91/19711, WO91/19712, WO94/27988 and WO95/01977.

In a non-limiting embodiment, the ratio between the small carboxylic acid molecules such as succinic acid, or salts thereof, and the PPI is from about 20:1 to about 2:1, preferably from about 10:1 to about 5:1. More preferably the ratio between the small carboxylic acid molecules, or salts thereof and the PPI is 8:1 to 6:1, e.g., 7.5:1. According to one preferred embodiment, the PPI used in the present invention is enteric-coated.

The compositions of the present invention are preferably suitable for oral administration. The PPI particles in the oral compositions according to the present invention are preferably enteric-coated. The preparation of enteric-coated particles comprising a PPI such as Omeprazole is disclosed for example in U.S. Pat. Nos. 4,786,505 and 4,853,230.

The compositions of the present invention comprise a PPI in an effective amount to achieve a pharmacological effect or therapeutic improvement without undue adverse side effects. A therapeutic improvement includes but is not limited to: raising of gastric pH, reduced gastrointestinal bleeding, or improvement or elimination of symptoms. According to a preferred embodiment, the typical daily dose of the PPI varies and will depend on various factors such as the individual requirements of the patients and the disease to be treated. In general, the daily dose of PPI will be in the range of 1-400 mg. A preferred standard approximate amount of a PPI present in the composition is typically about 20-80 mg of omeprazole, about 30-60 mg lansoprazole, about 40-80 mg pantoprazole, about 20-40 mg rabeprazole, and the pharmacologically equivalent doses of the following PPIs: habeprazole, pariprazole, dontoprazole, ransoprazole, perprazole (s-omeprazole magnesium), tenatoprazole and leminoprazole.

The active ingredients of the present invention are preferably formulated in a single oral dosage form containing all active ingredients. The compositions of the present invention may be formulated in either solid or liquid form. It is noted that solid formulations are preferred in view of the improved stability of solid formulations as compared to liquid formulations and better patient compliance.

In one embodiment, the PPI particles and one or more small carboxylic acids are formulated in a single solid dosage form such as multi-layered tablets, suspension tablets, effervescent tablets, powder, pellets, granules or capsules comprising multiple beads or physically separated from one another in a capsule within a capsule form. In another embodiment, the active agents may be formulated in a single liquid dosage form such as suspension containing all active ingredients or dry suspension to be reconstituted prior to use.

The acid-labile PPI particles in the present composition are preferably formulated as enteric-coated delayed-release granules in order to avoid contact with the acidic gastric juice. However, the small carboxylic acids of the present invention may be formulated either in an immediate-release formulation for release in the stomach, or in a delayed-release or extended release formulation in the stomach to better synchronize with PPI activity. For example, if enteric-coated PPI particles are used resulting in delayed absorption in blood, it may be desirable that the release of the small carboxylic acids in the stomach be delayed or extended. In a specific embodiment, the PPI particles are coated with enteric-coated layer so as the absorption of the PPI in blood is preferably delayed by between 60-120 min, and the small carboxylic acid particles to be released in the stomach so that the release of the small carboxylic acids is synchronized with the absorption of the PPI. Preferably the release of the small carboxylic acid particles in the stomach is delayed by 10-80 min, more preferably by 10-30 min.

Non-limiting examples of suitable enteric-coated polymers to be used in the present invention are: cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. A suitable commercially available enteric material, for example, is sold under the trademark Eudragit L 100-55. This coating can be spray coated onto the substrate.

Non-enteric-coated time-dependent release polymers include, for example, one or more polymers that swell in the stomach via the absorption of water from the gastric fluid, thereby increasing the size of the particles to create thick coating layer. The time-dependent release coating generally possesses erosion and/or diffusion properties that are independent of the pH of the external aqueous medium. Thus, the active ingredient is slowly released from the particles by diffusion or following slow erosion of the particles in the stomach.

The erosion properties of the polymer in the stomach resulting from the interaction of fluid with the surface of the dosage form are determined mainly by the polymer molecular weight and the drug/polymer ratio. In order to ensure a delay of between about 10 min to about 60 min in the release of the small carboxylic acids in the stomach, it is recommended that the molecular weight of the polymer be in the range from about $10^5$ to about $10^7$ gram/mol.

Suitable non-enteric time-dependent release coatings are for example: film-forming compounds such as cellulosic derivatives, such as methylcellulose, hydroxypropyl methylcellulose (HPMC), hydroxyethylcellulose, and/or acrylic polymers including the non-enteric forms of the Eudragit brand polymers. Other film-forming materials may be used alone or in combination with each other or with the ones listed above. These other film forming materials generally include poly(vinylpyrrolidone), Zein, poly(ethylene glycol), poly(ethylene oxide), poly(vinyl alcohol), poly(vinyl acetate), and ethyl cellulose, as well as other pharmaceutically acceptable hydrophilic and hydrophobic film-forming materials. These film-forming materials may be applied to the substrate cores using water as the vehicle or, alternatively, a solvent system. Hydro-alcoholic systems may also be employed to serve as a vehicle for film formation.

Other materials which are suitable for making the time-dependent release coating of the invention include, by way of example and without limitation, chitosan and related derivatives such as N-trimethylene chloride chitosan or chitosan esters, such as chitosan succinate and chitosan phthalate, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives such as a member selected from the group consisting of hydroxyethyl methylcellulose, hydroxypropyl methylcellulose, and hydroxybutyl methylcellulose; other cellulose polymers such as sodium carboxymethylcellulose; and other materials known to those of ordinary skill in the art. Other lamina forming materials that can be used for this purpose include poly(vinylpyrrolidone), polyvinylalcohol, polyethylene oxide, a blend of gelatin and polyvinyl-pyrrolidone, gelatin, glucose, saccharides, povidone, copovidone, poly(vinylpyrrolidone)-poly(vinyl acetate) copolymer.

In one specific example, the composition of the present invention is formulated as a single dosage form comprising multiple beads contained in hard gelatin capsules. The capsules contain mixed population of beads selected from: beads comprising enteric-coated PPI or beads comprising PPI coated with time-dependent release polymer, and beads comprising one or more small carboxylic acids that may be coated with either hydroxypropyl methylcellulose or alginate for release in the stomach. The rate of the carboxylic acids release is determined by the thickness and the erosion rate of the hydroxypropyl methylcellulose. Extending or delaying the release of the small carboxylic acids in the stomach may be achieved by using solid forms of the small carboxylic acids (e.g crystalline powders) and/or polymer coating of the small carboxylic acids and/or by the final formulation properties (e.g. release of the small carboxylic acids from a matrix or a capsule).

In yet another example, the compositions of the present invention are formulated as press-coat or double-layered tablets comprising enteric-coated PPI in one layer and small carboxylic acids coated with hydroxypropyl methylcellulose for release in the stomach in a second layer.

In a further example, the compositions of the present invention may be formulated as two layer non-aqueous semi-solid fill into hard gelatin capsules in which the PPI is solubilized in a lipid base (non-aqueous, quick release) which is liquid above room temperature but forms a semi-solid on cooling and can therefore be filled into hard gelatin capsules.

In a further example, the compositions of the present invention may be formulated as an inner capsule filled with granules or pellets of succinic acid (as an example of small carboxylic acids) incorporated into an outer capsule filled with enteric-coated PPI granules (CapInCap formulation). Such formulation enables the release of PPI granules first from the outer capsule and a delayed-release of the succinic acid granules or pellets from the inner capsule.

In yet another example, the compositions of the present invention may be formulated as an inner capsule filled with granules or pellets of PPI incorporated into an outer capsule filled with succinic acid crystalline powder, granules or pellets.

The active ingredients of the present invention may be formulated in a multiple oral dosage forms in which the small carboxylic acids are administered in a separate dosage form but in conjugation with the PPI. For example, the small carboxylic acids may be formulated in oral suspension or a solid dosage form such as capsules, tablets, suspension tablets, or effervescent tablets and the PPI may be formulated in a separate solid dosage form, preferably enteric-coated beads or time-dependent release beads contained in capsules or tablets.

When using multiple oral dosage forms, the small carboxylic acids can be administered before, simultaneously with, or after the PPI. In sequential administration, there may be some substantial delay (e.g., minutes or even few hours) between the administration of the small carboxylic acids and the PPI as long as the small carboxylic acids have exerted some physiological effect when the PPI is administered or becomes active. In a preferred embodiment, the PPI administered is in the enteric-coated or the time-dependent release form. According to this embodiment, it is preferable that the PPI administration precedes the small carboxylic acids administration by 10 to 60 minutes in order to ensure that the PPI absorbed in the proximal part of the small intestine will be available for inhibiting the $H^+/K^+$-ATPase pumps while the small carboxylic acids are still active in the stomach.

Prolonging the retention time, if needed, of the small carboxylic acids in the stomach is possible for example by using dosage forms that unfold rapidly within the stomach to a size that resists gastric emptying. Such systems retain their integrity for an extended period and will not empty from the stomach at all until breakdown into small pieces occurs. Caldwell (Caldwell, L. J., Gardener, C. R., Cargill, R. C. (1988), U.S. Pat. No. 4,767,627) describes a cross shaped device made of erodible polymer and loaded with drug which is folded and inserted into a hard gelatin capsule. Following oral administration the gelatin shell disintegrates and the folded device opens out. With a minimum size of 1.6 cm and a maximum size of 5 cm it will not pass from the stomach through the pylorus until the polymer erodes to the point where the system is sufficiently small that it can be passed from the stomach.

An alternative approach to prolong the retention time of the small carboxylic acids in the stomach is to use a hydrophilic erodible polymer system such as Poly(ethylene oxide) (Polyox) and Hydroxypropyl-methylcellulose (HPMC) that is of a convenient size for administration to humans. On imbibing fluid the system swells over a short period of time to a size that will encourage prolonged gastric retention, allowing sustained release of contained drug in the stomach.

The active ingredients of the present invention may be incorporated within inert pharmaceutically acceptable beads. In this case, the drug(s) may be mixed with further ingredients prior to being coated onto the beads. Ingredients include, but are not limited to, binders, surfactants, fillers, disintegrating agents, alkaline additives or other pharmaceutically acceptable ingredients, alone or in mixtures. Binders include, for example, celluloses such as hydroxypropyl methylcellulose, hydroxypropyl cellulose and carboxymethyl-cellulose sodium, polyvinyl pyrrolidone, sugars, starches and other pharmaceutically acceptable substances with cohesive properties. Suitable surfactants include pharmaceutically acceptable non-ionic or ionic surfactants. An example of a suitable surfactant is sodium lauryl sulfate.

The particles may be formed into a packed mass for ingestion by conventional techniques. For instance, the particles may be encapsulated as a "hard-filled capsule" using known encapsulating procedures and materials. The encapsulating material should be highly soluble in gastric fluid so that the particles are rapidly dispersed in the stomach after the capsule is ingested.

In another embodiment, the active ingredients of the present invention are packaged in compressed tablets. The term "compressed tablet" generally refers to a plain, uncoated tablet for oral ingestion, prepared by a single compression or by pre-compaction tapping followed by a final compression. Such solid forms can be manufactured as is well known in the art. Tablet forms can include, for example, one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmaceutically compatible carriers. The manufacturing processes may employ one, or a combination of, four established methods: (1) dry mixing; (2) direct compression; (3) milling; and (4) non-aqueous granulation. Lachman et al., The Theory and Practice of Industrial Pharmacy (1986). Such tablets may also comprise film coatings, which preferably dissolve upon oral ingestion or upon contact with diluent.

In another alternative, the compositions of the present invention are formulated in compressed forms, such as suspension tablets and effervescent tablets, such that upon reaction with water or other diluents, the aqueous form of the composition is produced for oral administration. These forms are particularly useful for medicating children and the elderly and others in a way that is much more acceptable than swallowing or chewing a tablet. The present pharmaceutical tablets or other solid dosage forms disintegrate the alkaline agent with minimal shaking or agitation.

The term "suspension tablets" as used herein refers to compressed tablets which rapidly disintegrate after they are placed in water, and are readily dispersible to form a suspension containing a precise dosage of the active ingredients. To achieve rapid disintegration of the tablet, a disintegrant such as croscarmellose sodium may be added to the formulation. The disintegrant may be blended in compressed tablet formulations either alone or in combination with microcrystalline cellulose, which is well known for its ability to improve compressibility of difficult to compress tablet materials. Microcrystalline cellulose, alone or co-processed with other ingredients, is also a common additive for compressed tablets and is well known for its ability to improve compressibility of difficult to compress tablet materials. It is commercially available under the Avicel trademark.

In addition to the above ingredients, the oral dosage forms described above may also contain suitable quantities of other materials, e.g. diluents, lubricants, binders, granulating aids, colorants, flavorants and glidants that are conventional in the pharmaceutical art. The quantities of these additional materials will be sufficient to provide the desired effect to the desired formulation. Specific examples of pharmaceutically acceptable carriers and excipients that may be used to formulate oral dosage forms are described in the Handbook of Pharmaceutical Excipients, American Pharmaceutical Association (1986), incorporated by reference herein.

For parenteral administration of the PPI, it may be administered either by intravenous, subcutaneous or intramuscular injection, in compositions with pharmaceutically acceptable vehicles or carriers. For administration by injection, it is preferred to use the active ingredients in solution in a sterile aqueous vehicle, which may also contain other solutes such as buffers or preservatives as well as sufficient quantities of pharmaceutically acceptable salts or of glucose to make the solution isotonic with respect to blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxyethylene sorbitol, and sorbitan esters. Sodium chloride, glucose or glycerol may be incorporated into a therapeutic agent in an amount sufficient to prepare an isotonic solution. The therapeutic agent may further contain ordinary dissolving aids, buffers, and preservatives, and optionally, coloring agents, fragrances, flavors, sweeteners, and other pharmacologically active agents which are known in the art.

In another preferred embodiment, the composition of the present invention further comprises one or more of pro-kinetic or pro-motility agents and alginates. Pro-kinetic or pro-motility or other anti-reflux agents to be used in the present invention are for example: erythromycin derivatives, Baclofen, Metoclopramide, Domperidone, Erythromycin, Mitemcinal, Cisapride, Mosapride, Tegaserod and Octreotide. Alginates to be used in the present invention are for example: sodium, potassium and magnesium alginates.

The present compositions may further comprise an antibiotic effective against bacteria residing in the stomach, specifically an antibiotic/s or anti-bacterial for the treatment of ulcers associated with *Helicobacter* sp infection (e.g. *Helicobacter pylori*). Such antibiotics include, for example, amoxicillin, clarithromycin or other macrolides, metronidazole and related antibiotics, tetracycline, quinolones, rifabutin or furazolidone.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Stimulation of Gastric Acid Secretion Following Oral Administration of Sodium Succinate in Rats Rats were administered (per os) with 15 mg/kg of sodium succinate using gavage. 30 minutes later the rats were anesthetized with ketamine/domitor and the pylorus was ligated. Following additional 60 min, gastric juice was collected from the gastric lumen. Acid output was determined by titration with NaOH. Total acid output expressed in mEq HCl was calculated by multiplying the sample volume by the acid concentration. Results are expressed as means±SEM of 12 animals from each experimental group. As demonstrated in FIG. 1, oral administration of sodium succinate significantly enhanced gastric acid secretion in pylorus-ligated rats.

Example 2

Succinic Acid is Capable of Enhancing the Inhibitory Effect of Pantoprazole on Gastric Acid Secretion To study the effect of succinic acid on the inhibition of gastric acid secretion by pantoprazole, an experimental model of conscious pylorus-ligated rats was used. This experimental model permits the analysis of the effect of drugs on gastric acid secretion in conscious animals and avoids the effect of anesthesia on gastric acid secretion. Pantoprazole alone (10 mg/ml) and in combination with succinic acid (15 mg/ml) were administered by oral gavage. Water was administered as a placebo. 15 minutes later the animals were anesthetized using anesthetic gas machine for a short period (5 minutes) that is sufficient to perform the pylorus ligation procedure and to close the abdomen. The animals were then placed back into its cage for additional 90 min after which the animals were sacrificed. The ligature was placed around the esophagus, the stomach removed and gastric content was collected. Following centrifugation, the gastric output and the pH of the gastric juice samples was determined. Data is presented as mean±SD of gastric output and pH values. The number of animals is 4-8 in each experimental group.

Figure 2:
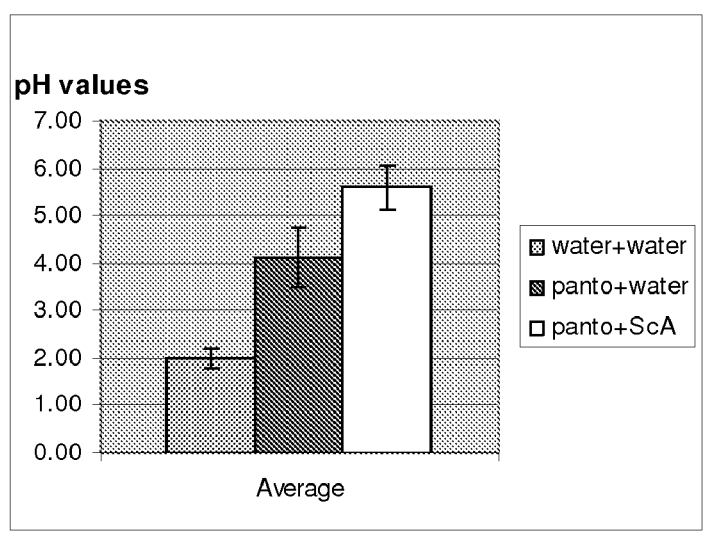
FIG. 2 demonstrates that the administration of pantoprazole (panto) with succinic acid (ScA) resulted in higher pH values in the gastric juice samples as compared to pantoprazole alone.
Figure 3:
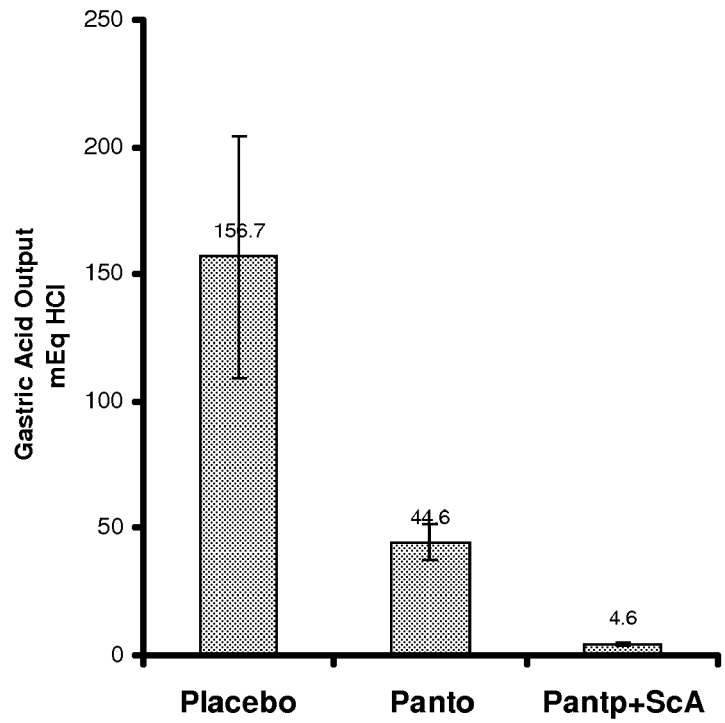
FIG. 3 demonstrates that the administration of pantoprazole with succinic acid (panto-ScA) resulted in lower values of gastric output in the stomach as compared to pantoprazole alone (panto).
Figure 4:
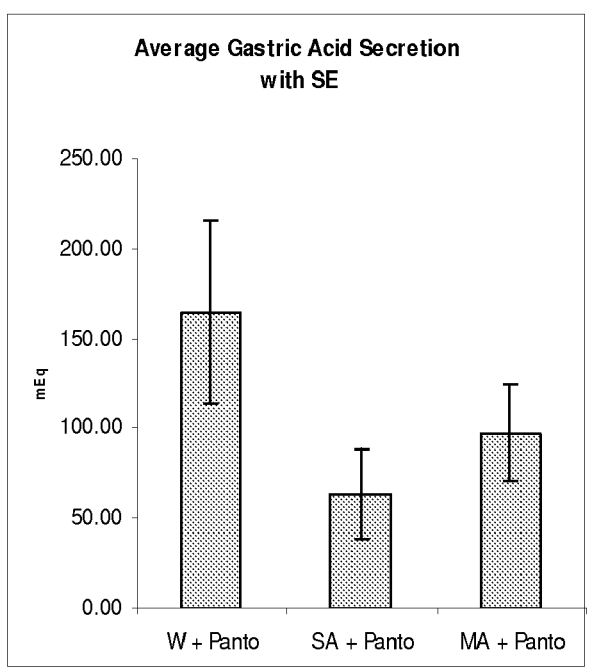
FIG. 4 demonstrates that both succinic and maleic acids may facilitate the effect of Pantoprazole on gastric acid secretion.

As can be seen in FIG. 2, the administration of pantoprazole (panto) with succinic acid (ScA) resulted in higher pH values in the gastric juice samples as compared to pantoprazole alone. FIG. 3 further demonstrates that the administration of pantoprazole with succinic acid resulted in lower values of gastric output in the stomach as compared to pantoprazole alone. These results indicate that succinic acid increases the efficacy of pantoprazole in inhibiting gastric acid secretion. As shown in FIG. 4, maleic acid (14.7 mg/kg) also enhanced the inhibitory effect of pantoprazole (3 mg/kg) on gastric acid secretion.

Figure 5:
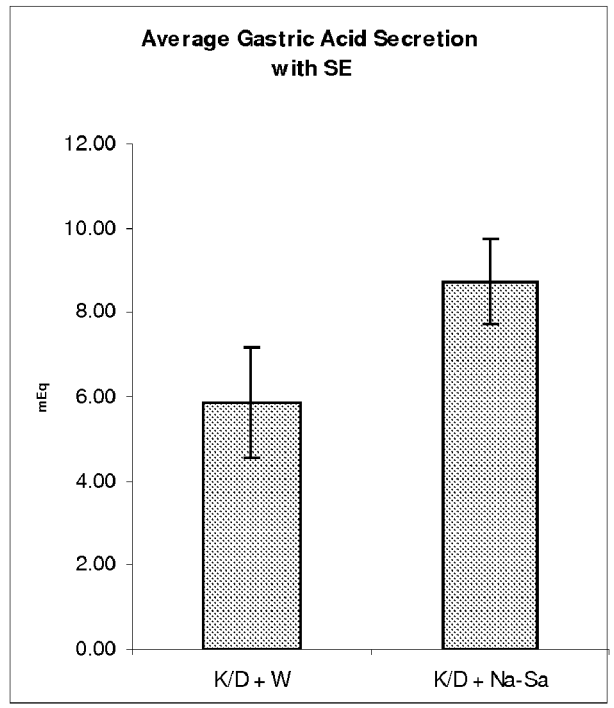
FIG. 5 demonstrates that succinic acid is capable of inducing gastric acid secretion when administered to pylorus-ligated rats.

The possibility that succinic acid induces gastric acid secretion via local effect on the gastric lumen was tested in animals in which sodium succinate was administered after the ligation of the pylorus. In these conditions, sodium succinate can exert local effect within the stomach. As demonstrated in FIG. 5, sodium succinate is capable of inducing acid secretion if administered after ligation, probably via local effect on the gastric lumen.

Example 3

The Effect of Omeprazole (40 mg) Combined with Succinic Acid (600 or 300 mg) Compared to Omeprazole Only on Inhibition of Gastric Acid Secretion in Human Subjects The clinical study was aimed to compare the effect of Omeprazole treatment (40 mg) combined with Succinic Acid (600 mg) administered at bedtime compared to Omeprazole only on inhibition of nocturnal gastric acid secretion. *H. pylori* negative healthy human volunteers, (n=9) were administered with Omeprazole (Prilosec® 40 mg) together with Succinic Acid (600 mg in capsules) at bedtime without a meal for six days. Succinic Acid was administered one hour following Omeprazole administration. Gastric pH was measured on Day 1 and 5 using a pH probe. The pH probe was inserted into the distal portion of the stomach and located 20 cm below the lower esophageal sphincter. Baseline measurements of gastric pH were performed before omeprazole administration and during the following 24 hours. Standard meals were administered during pH monitoring. Blood samples for $P_K$ analysis of Omeprazole were drawn on Day 1 and 5. After a washout period of at least 14 days, the same subjects were administered with Omeprazole 40 mg alone. The results obtained with 7 human subjects are summarized in Table 1 below. The results are expressed as the average (n=7) percent of time with gastric pH above 4 at night following bed-time administration of Omeprazole 40 mg and Succinic acid 600 mg versus Omeprazole 40 mg alone in Day 1 and Day 5 of treatment. These results indicate that the treatment with Omeprazole 40 mg in combination with Succinic acid 600 mg exhibited higher percentage of time with pH above 4 during nighttime compared to Omeprazole 40 mg alone.

TABLE 1

The average (n = 7) percent of time with gastric pH above 4 following bed-time administration of Omeprazole 40 mg and Succinic acid 600 mg versus Omeprazole 40 mg alone.

| Treatment | 12:00-2:00 AM (% time pH > 4) | 2:00-4:00 AM (% time pH > 4) | 4:00-6:00 AM (% time pH > 4) |
|---|---|---|---|
| Omeprazole 40 mg and Succinic acid 600 mg- Day 1 | 18.98 | 41.48 | 74.87 |

TABLE 1-continued

The average (n = 7) percent of time with gastric pH above 4 following bed-time administration of Omeprazole 40 mg and Succinic acid 600 mg versus Omeprazole 40 mg alone.

| Treatment | 12:00-2:00 AM (% time pH > 4) | 2:00-4:00 AM (% time pH > 4) | 4:00-6:00 AM (% time pH > 4) |
|---|---|---|---|
| Omeprazole 40 mg alone | 29.57 | 32.72 | 52.30 |
| Omeprazole 40 mg and Succinic acid 600 mg- Day 5 | 51.77 | 70.05 | 83.61 |
| Omeprazole 40 mg alone | 52.31 | 53.11 | 64.94 |

In a further clinical study; healthy human volunteers were administered with Omeprazole and SA capsules which were co-administered at bed-time: Treatment T1-40 mg Omeprazole plus 600 mg SA; Treatment T2-40 mg Omeprazole plus 300 mg SA; Treatment T3-20 mg Omeprazole plus 300 mg SA. The study included gastric pH measurements on day 1 (first dose), day 3 (third dose) and day 5 (fifth dose). The results of this study are summarized in Table 2 below. Study medications were administered at 10:00 pm on empty stomach and pH measurements were recorded for 24 hrs. The percentage time of gastric pH above 4 following the administration of SA and Omeprazole was calculated after the first dose, the third dose and the fifth dose. As demonstrated below, co-administration of Omeprazole and SA capsules was superior over a 1 hour interval (in terms of % time with gastric pH>4) both for total 24 h analysis and for the nocturnal hours only, as of the first dose.

The values obtained with 300 mg SA and 40 mg Omeprazole were superior to the 40 mg Omeprazole alone. Interestingly, the results obtained following the third dose of 300 mg SA and 40 mg Omeprazole are comparable to the results following the fifth dose of 300 mg SA and 40 mg Omeprazole. This data implies that co-administration of Omeprazole and SA capsules provides the means to reach steady state conditions earlier than with the current treatment with PPI (usually at day 7).

TABLE 2

The average percent of time with gastric pH above 4 following bed-time simulteneous administration of Omeprazole (40 mg or 20 mg) and Succinic acid (600 mg or 300 mg) versus Omeprazole 40 mg alone.

| Treatment | 40 mg Omeprazole | 40 mg Omeprazole plus 600 mg SA (T1) | 40 mg Omeprazole plus 300 mg SA (T2) | 20 mg Omeprazole (T3) |
|---|---|---|---|---|
| % time with pH > 4 (total 24 h) | First dose: 41% Fifth dose: 64% | First dose: 56% Third dose: 74% Fifth dose: 76% | First dose: 61% Third dose: 86% Fifth dose: 87% | First dose: 38% Third dose: 64% Fifth dose: 55% |
| % time with pH > 4 (nocturnal hours only) | First dose: 25% Fifth dose: 49% | First dose: 28% Third dose: 53% Fifth dose: 52% | First dose: 34% Third dose: 71% Fifth dose: 75% | First dose: 21% Third dose: 58% Fifth dose: 28% |

Example 4

Succinic Acid (600 mg) in a Capsule Formulation Exhibits Delayed Effects on Inducing Gastric Acid Output (GAO) in Human Subjects The effect of Succinic Acid alone (600 mg) administered in capsule versus solution on gastric acid output was assessed in human subjects after an overnight fast. Nine eligible *H. pylori* negative, normal acid secreting subjects (defined by maximal acid output of 10-60 mEq/hr), were treated by the study medication in an open, dose-ranging, paired study. Succinic Acid was administered in 2 different oral formulations: A solution (600 mg of Succinic Acid dissolved in 160 mL water administered via a nasogastric tube into the stomach) and a solid dosage form in the form of a capsule (single dose of 600 mg per capsule administered orally with 160 mL water). Gastric acid output was measured using a nasogastric tube positioned in the stomach by collecting successive samples of gastric acid at the end of the 25 min exposure to Succinic Acid and at short time intervals following the aspiration of Succinic Acid (additional 90 min post Succinic acid aspiration).

As demonstrated in Table 3 below, 600 mg Succinic Acid (SA) in capsules exhibited the maximum gastric acid output between 30-60 min from SA administration while SA in solution exhibited the maximum effect between 0-30 min from dosing. Therefore, SA in capsules exhibited a delayed effect on gastric acid output compared to the solution as measured during 90 min from dosing. These results indicate that it is possible to delay the effect of SA on gastric acid secretion by using capsules of SA instead of solution.

TABLE 3

The average (n = 9) gastric acid output (GAO, in mEq HCl) induced by 600 mg SA formulated in capsules versus solution

|  | GAO (mEq HCl) 0-30 min from SA administration (Average ± SEM) | GAO (mEq HCl) 30-60 min from SA administration (Average ± SEM) | GAO (mEq HCl) 60-90 min from SA administration (Average ± SEM) |
| --- | --- | --- | --- |
| 600 mg SA in capsules | 4.47 ± 1.7 | 8.12 ± 0.98 | 3.40 ± 1.19 |
| 600 mg SA in solution | 9.05 ± 2.17 | 5.24 ± 1.95 | 1.47 ± 1.03 |

Example 5

Dissolution Profile of Succinic Acid Formulated in Cap-in-Cap Formulation Versus Single Capsule and Free Powder The dissolution test was done in 1000 ml 0.1N HCl, pH-1.2 at 37° C. mixed by paddle at 75 RPM. Sampling was done at 2, 4, 6, 10, 20 and 30 min. Samples were filtered and diluted 1:1 in water and analyzed by HPLC for succinic acid quantification. The dissolution test was repeated on 6 capsules in each group: Group 1-300 mg succinic acid Free powder (without capsule); group 2-300 mg SA in size "3" capsules; group 3-300 mg succinic acid in size "3" capsules inserted in size "00" capsules containing 20 mg Omeprazole granules (Cap-in-Cap).

Figure 6:
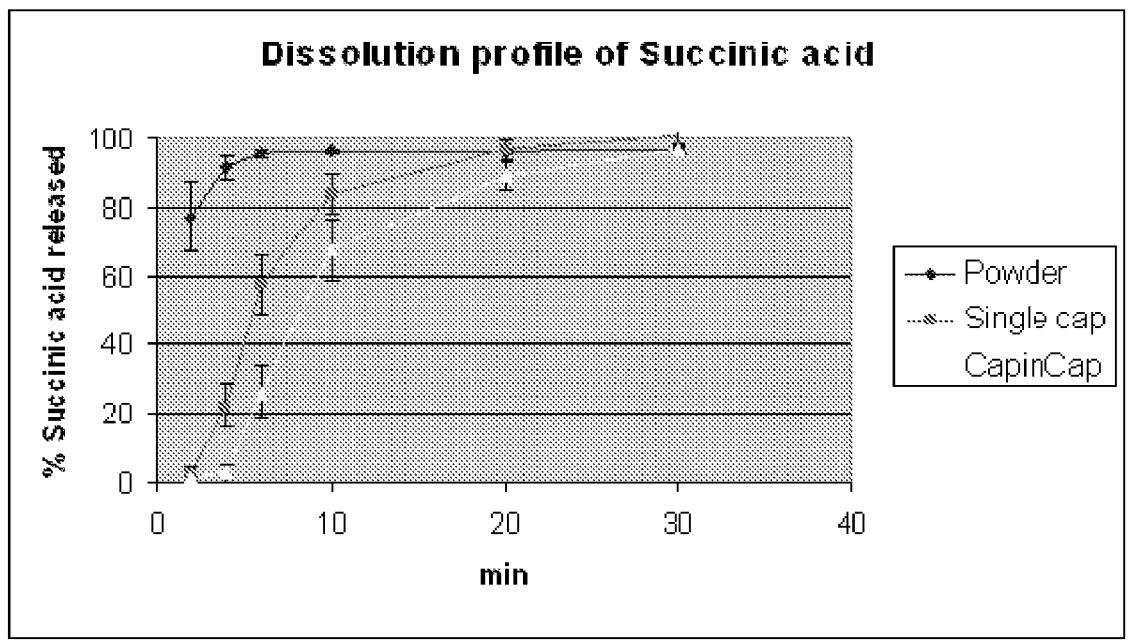
FIG. 6 demonstrates the dissolution profile of succinic acid formulated in Cap-in-Cap formulation versus single capsule and free powder.

As seen in Table 4 below and in FIG. 6, full dissolution of succinic acid is delayed by approximately 15 min when formulated in a single capsule (compared to free powder). The dissolution of succinic acid is delayed by an additional 8-10 min when formulated in a Cap-in-Cap formulation. These results demonstrate that Cap-in-Cap formulation provides delayed release of succinic acid which is beneficial in delaying the release of succinic acid in the stomach.

TABLE 4

Dissolution profile of succinic acid in different formulations

| Time (min) | % SA Released Powder | % SA Released Single cap | % SA Released CapinCap |
| --- | --- | --- | --- |
| 2 | 77.2 | 2.5 | 1.3 |
| 4 | 91.4 | 22 | 2.7 |
| 6 | 95.4 | 57.3 | 25.6 |
| 10 | 96.1 | 83.7 | 67.6 |
| 20 | 96.3 | 96.5 | 88.6 |
| 30 | 96.4 | 100.5 | 96.6 |

Example 6

Oral Formulations Comprising a Proton Pump Inhibitor (PPI) and Succinic Acid Hard Gelatin Capsules Hard gelatin capsules may contain a mixed granules population of succinic acid (SA) and PPI. SA granules are in an immediate release or delayed release formulation for release in the stomach and PPI is formulated as enteric-coated granules or time-dependent release coating (delayed release). Granules may be packed into a hard gelatin capsule in an amount corresponding to 40 mg PPI and 600 or 300 mg SA per capsule.

A) Immediate Release SA Formulation:
   40 mg enteric-coated (Eudragit) or time-dependent release coated (HPMC) PPI granules
   600 or 300 mg SA granules
   Diluent B) Delayed release SA formulation:
   40 mg enteric-coated or time-dependent release coated PPI granules
   600 or 300 mg SA granules (HPMC coated)
   diluent For the delayed release SA formulation, SA solution is sprayed on inert beads in a fluid bed apparatus. After drying, the SA beads are further coated with hydroxypropyl methylcellulose (HPMC) to form the final granules. The rate of SA release is determined by the thickness and erosion rate of the HPMC layer. SA is aimed to be released from the coated beads 10 min following administration.

Tablets or Caplets

The pharmaceutical composition may be in the form of tablet or more preferably caplet. The caplet contains a mixed granules population of SA (immediate release or delayed release in the stomach, as mentioned above), enteric-coated or time-dependent release coated PPI (stable under compression pressure) and a wide variety of conventional tableting aid agents to be compressed into a caplet formulation.

Minitabs in Hard Gelatin Capsule (Gastric Retentive Dosage Form)

SA are granulated with a combination of Polyox WSR N60 and HPMC K100M. These granules are further combined with lactose and HPMC and later on compressed into mini-tabs with the ability of fast swelling into size, big enough to enable gastric retention. The polymeric matrix controls the SA release into the stomach.

The SA mini-tabs are mixed with enteric-coated PPI pellets and filled into hard gelatin capsules. Following disintegration of the capsules gelatinic body, the PPI pellets pass though the stomach to the duodenum, where the enteric coat will dissolve. The SA mini-tabs remain in the stomach and slowly release their content in a controlled release gastro retentive manner.

Capsule in Capsule (Cap-in-Cap) Formulation

An inner capsule filled with granules or pellets of either succinic acid or enteric coated PPI, incorporated into an outer capsule filled with enteric-coated PPI granules or succinic acid.

Press Coated Tablet

The tablet's internal core is composed of SA combined with a mixture of hydrogels aimed for controlled release and prompt swelling of the dosage form in the stomach. The expanded core has gastro-retentive properties. Mixtures of gums like: xantan gum, gellan gum, together with cellulose derivatives such as sodium carboxymethylcellulose or HPMC may be applied.

The core is further coated with an external layer composed of enteric-coated PPI pellets (stable under compression pressure) together with appropriate filler, which disintegrates immediately after digestion and promptly releases the PPI. The final product is a tablet composed of an internal controlled-release core of SA and an outer layer with the enteric-coated or time-dependent release coated PPI.

Pulsatile Release Dosage Forms

Hard gelatin capsules are filled with:
a) SA granules, combined with HPMC K100M and Vitamin E-TPGS combined together with sodium chloride (osmotic agent, to attract water into the capsule).
b) Expansion layer with a mixture of hydrogels like Polyox WSR N60, carboxymethylcellulose.
c) Enteric-coated or time-dependent release coated PPI pellets.

The capsule body is coated with non-soluble coating layer such as ethyl cellulose or cellulose acetate. After digestion, the mid layer will get hydrated and expanded, to prompt the release of the enteric-coated PPI pellets into the stomach. The SA will remain in the capsule body, which will act as a gastro retentive controlled release dosage form, while the release is controlled by the hydrogel layer.

Powder for Oral Suspension

Powder for oral suspension is comprised of SA and enteric-coated or time-dependent release coated PPI granules. SA granules may be in immediate release or delayed release formulation for release in the stomach (as mentioned above). PPI are formulated as enteric-coated or time-dependent release coated granules (delayed release). The composition comes in individual packets to be constituted with water. When mixed with water, powder becomes a uniform liquid suspension.

Injectable Preparation

A PPI liquid solution is prepared by dissolving in phosphate-buffered saline. To prepare a physiological phosphate-buffered saline solution for dissolution of PPI, a concentrated (20 times) solution of phosphate buffered saline (PBS) is diluted to obtain a 1× solution. The 20 times PBS solution is prepared by dissolving the following reagents in sufficient water to make 1,000 ml of solution: sodium chloride, 160 grams; potassium chloride, 4.0 grams; sodium hydrogen phosphate, 23 grams; potassium dihydrogen phosphate, 4.0 grams; and optionally phenol red powder, 0.4 grams. The PBS solution is then sterilized by autoclaving at 15 pounds of pressure for 15 minutes and is diluted with additional sterile water to a 1 times concentration prior to dissolution of the PPI. To prepare a dose form for intravenous administration, PPI is dissolved in 1 times PBS at concentrations of 0.2 mg, and the resulting solution (200 ml) is dispensed into sealable translucent plastic bags for use in intravenous administration. These steps are performed under sterile conditions.

It will be appreciated by a person skilled in the art that the present invention is not limited by what has been particularly shown and described hereinabove. Rather, the scope of the invention is defined by the claims that follow.

What is claimed is:

1. A multiple unit pharmaceutical composition, wherein the active ingredients of said composition consist of a pharmaceutically effective amount of: (i) a parietal cell activator, wherein the parietal cell activator is one or more small carboxylic acid molecules, or any salts thereof, wherein the small carboxylic acid molecules or any salts thereof are saturated or non-saturated monocarboxylic, dicarboxylic, or tricarboxylic acid molecules or any salts thereof having between three to six carbon atoms selected from the group consisting of maleic acid, succinic acid, citric acid, pyruvate, fumarate, alpha ketoglutarate, succinyl-CoA and oxaloacetate; and (ii) an enteric-coated irreversible gastric $H^+/K^+$-ATPase proton pump inhibitor (PPI) formulated for absorption in the small intestine, wherein the parietal cell activator is in an amount between 200 to 600 mg and the PPI is omeprazole in an amount of 20 to 80 mg, wherein the composition is suitable for administration to a human patient, wherein the composition disintegrates in the stomach and the release of the active ingredients is controlled such that the activity of the PPI is synchronized with the parietal cell activity, wherein the parietal cell activator is released in the stomach in an amount sufficient to reduce gastric acid secretion in conjunction with the PPI, and wherein the enteric-coated PPI and the parietal cell activator are physically separated within the multiple unit composition.

2. The composition of claim 1, wherein the composition additionally contains one or more prokinetic agents, alginates or antibiotics.

3. The composition of claim 2, wherein the prokinetic agent is selected from the group consisting of erythromycin derivatives, baclofen, metoclopramide, domperidone, erythromycin, mitemcinal, cisapride, mosapride, tegaserod and octreotide.

4. The composition of claim 1, wherein the ratio between the parietal cell activator or salts thereof, and the PPI is from about 20:1 to about 2:1.

5. The composition of claim 1, wherein at least 50% of the parietal cell activator or salts thereof are released in the stomach.

6. A method of reducing gastric acid secretion in a human subject in need thereof, the method comprising administering to the human subject a multiple unit pharmaceutical composition, wherein the active ingredients of said composition consist of a pharmaceutically effective amount of: (i) a parietal cell activator, wherein the parietal cell activator is one or more small carboxylic acid molecules, or any salts thereof, wherein the small carboxylic acid molecules or any salts thereof are saturated or non-saturated monocarboxylic, dicarboxylic, or tricarboxylic acid molecules or any salts thereof having between three to six carbon atoms selected from the group consisting of maleic acid, succinic acid, citric acid, pyruvate, fumarate, alpha ketoglutarate, succinyl-CoA and oxaloacetate and (ii) an enteric-coated irreversible gastric $H^+/K^+$-ATPase proton pump inhibitor (PPI) formulated for absorption in the small intestine, wherein the parietal cell activator is in an amount between 200 to 600 mg and the PPI is omeprazole in an amount of 20 to 80 mg, wherein the composition is suitable for administration to a human patient, wherein the composition disintegrates in the stomach and the release of the active ingredients is controlled such that the activity of the PPI is synchronized with the parietal cell activity, wherein the parietal cell activator is released in the stomach in an amount sufficient to reduce gastric acid secretion in conjunction with the PPI, and wherein the enteric-coated PPI and the parietal cell activator are physically separated within the multiple unit composition, wherein the parietal cell activator is encapsulated in an internal capsule and the internal capsule is encapsulated within an external capsule which contains the enteric-coated PPI.

7. The method of claim 6, wherein the human subject has a disorder or symptoms selected from the group consisting of: nocturnal gastro-esophageal reflux disease (GERD) symptoms, reflux esophagitis, gastritis, duodenitis, gastric ulcer, duodenal ulcer, pathologies associated with nonsteroidal anti-inflammatory drugs (NSAID), non-ulcer Dyspepsia, gastro-esophageal reflux disease, gastrinomas, acute upper gastrointestinal bleeding, stress ulceration, *Helicobacter pylori* infections, Zollinger-Ellison syndrome (ZES), Werner's syndrome, and systemic mastocytosis.

8. A pharmaceutical composition comprising a first and second unit, the active ingredient of the first unit consisting of a parietal cell activator, wherein the parietal cell activator is one or more small carboxylic acid molecules, or any salts thereof, wherein the small carboxylic acid molecules or any salts thereof are saturated or non-saturated monocarboxylic, dicarboxylic, or tricarboxylic acid molecules or any salts thereof having between three to six carbon atoms selected from the group consisting of maleic acid, succinic acid, citric acid, pyruvate, fumarate, alpha ketoglutarate, succinyl-CoA and oxaloacetate, and the active ingredient of the second unit consisting of an enteric coated irreversible gastric $H^+/K^+$-ATPase proton pump inhibitor (PPI) formulated for absorption in the small intestine, wherein the small carboxylic acid molecules and enteric-coated PPI are physically separated, wherein the parietal cell activator is in an amount between 200 to 600 mg and the PPI is omeprazole in an amount of 20 to 80 mg, and wherein the composition is suitable for administration to a human patient, the first unit releasing at least 50% of the small carboxylic acid molecules in the stomach in an amount sufficient to activate parietal cells of a subject such that the activity of the PPI is synchronized with the parietal cell activity, wherein the carboxylic acid molecules in conjunction with the PPI reduces gastric acid secretion in the stomach, wherein the first unit is an internal capsule and the second unit is an external capsule, wherein the internal capsule is encapsulated within the external capsule.

9. The composition of claim 8, wherein at least 70% of the small carboxylic acid molecules are released in the stomach and the carboxylic acid molecules are succinic acid particles or any salts thereof.

10. The composition of claim 9, wherein the succinic acid particles are encapsulated in an internal capsule, the internal capsule is encapsulated within an external capsule which contains the enteric-coated PPI.

11. The composition of claim 9, wherein the enteric-coated PPI is encapsulated in an internal capsule, the internal capsule is encapsulated within an external capsule which contains the succinic acid particles.

12. A method of reducing gastric acid secretion in a human subject in need thereof, the method comprising administering to the human subject the composition of claim 8 in an amount sufficient to reduce gastric acid secretion in the human subject.

13. A pharmaceutical composition suitable for administration to a human patient, wherein the active ingredients of the composition consist of (i) a parietal cell activator, wherein the parietal cell activator is one or more small carboxylic acid molecules, or any salts thereof which activate parietal cells, wherein the small carboxylic acid molecules or any salts thereof are saturated or non-saturated monocarboxylic, dicarboxylic, or tricarboxylic acid molecules or any salts thereof having between three to six carbons selected from the group consisting of maleic acid, succinic acid, citric acid, pyruvate, fumarate, alpha-ketoglutarate, succinyl-CoA, and oxaloacetate; and (ii) an enteric coated irreversible gastric $H^+/K^+$-ATPase proton pump inhibitor (PPI), the parietal cell activator is in an amount between 200 to 600 mg and the PPI is omeprazole in an amount of 20 to 80 mg, wherein the ratio between the small carboxylic acid molecules and the PPI is from about 20:1 to about 2:1, the small carboxylic acid molecules being substantially released in the stomach in an amount sufficient to activate parietal cells located in the gastric lumen of a subject, wherein the carboxylic acid molecules enhances the activity of the PPI at reducing gastric acid secretion in the stomach, wherein the parietal cell activator is encapsulated in an internal capsule and the internal capsule is encapsulated within an external capsule which contains the enteric-coated PPI.

14. The composition of claim 13, wherein the ratio of small carboxylic acid moles to PPI is from about 10:1 to about 5:1 and the carboxylic acid molecules are succinic acid particles or any salts thereof.

15. A method of reducing gastric acid secretion in a human subject in need thereof, the method comprising administering to the human subject the composition of claim 13 in an amount sufficient to reduce gastric acid secretion in the human subject.

16. A pharmaceutical composition suitable for administration to a human patient, wherein the active ingredients of the composition consist of (i) a parietal cell activator, wherein the parietal cell activator is one or more small carboxylic acid molecules, or any salts thereof which activate parietal cells in a delayed release form, wherein the small carboxylic acid molecules or any salts thereof are saturated or non-saturated monocarboxylic, dicarboxylic, or tricarboxylic acid molecules or any salts thereof having between three to six carbons selected from the group consisting of maleic acid, succinic acid, citric acid, pyruvate, fumarate, alpha-ketoglutarate, succinyl-CoA, and oxaloacetate; and (ii) an enteric coated irreversible gastric $H^+/K^+$-ATPase proton pump inhibitor (PPI), wherein the parietal cell activator is in an amount between 200 to 600 mg and the PPI is omeprazole in an amount of 20 to 80 mg, wherein the carboxylic acid molecules are in a form for delayed release in the stomach, the small carboxylic acid molecules being substantially released in the stomach in an amount sufficient to activate parietal cells and the release being sufficiently delayed in the stomach to synchronize activation of the parietal cells with the absorption of the PPI in the small intestine to increase the effectiveness of the PPI, wherein the carboxylic acid molecules enhances the activity of the PPI at reducing gastric acid secretion in the stomach, wherein the parietal cell activator is encapsulated in an internal capsule and the internal capsule is encapsulated within an external capsule which contains the enteric-coated PPI.

17. The pharmaceutical compositions of claim 16, wherein the release of the small carboxylic acid molecule in the stomach is delayed by between 10 to 80 minutes to synchronize the release with absorption of the PPI in the blood.

18. The pharmaceutical composition of claim 17, wherein the carboxylic acid molecule is succinic acid or any salts thereof.

19. The composition of claim 16, wherein at least 70% of the small carboxylic acid molecules are released in the stomach.

20. The composition of claim 16, wherein the ratio between the small carboxylic acid molecules and the PPI is from about 20:1 to about 2:1.

21. The composition of claim 16, wherein at least 50% of parietal cells in the stomach are activated by the small carboxylic acid molecules and at least 100 mg is released in the stomach.

22. A method of reducing gastric acid secretion in a human subject in need thereof, the method comprising administering to the human subject the composition of claim 16 in an amount sufficient to reduce gastric acid secretion in the human subject.

* * * * *